(12) United States Patent
Conlon

(10) Patent No.: US 10,258,362 B2
(45) Date of Patent: Apr. 16, 2019

(54) ULTRASONIC SURGICAL INSTRUMENT WITH AD HOC FORMED BLADE

(71) Applicant: Ethicon Endo-Surgery, LLC, Guaynabo, PR (US)

(72) Inventor: Sean P. Conlon, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 113 days.

(21) Appl. No.: 15/207,637

(22) Filed: Jul. 12, 2016

(65) Prior Publication Data

US 2018/0014844 A1 Jan. 18, 2018

(51) Int. Cl.
| | |
|---|---|
| *A61B 17/32* | (2006.01) |
| *B33Y 10/00* | (2015.01) |
| *B23K 26/342* | (2014.01) |
| *A61N 7/00* | (2006.01) |
| *B22F 3/105* | (2006.01) |
| *B22F 5/00* | (2006.01) |
| *B33Y 80/00* | (2015.01) |

(Continued)

(52) U.S. Cl.
CPC ........... *A61B 17/320068* (2013.01); *A61B 17/320092* (2013.01); *A61N 7/00* (2013.01); *B22F 3/1055* (2013.01); *B22F 5/00* (2013.01); *B23K 26/342* (2015.10); *B33Y 10/00* (2014.12); *B33Y 80/00* (2014.12); *A61B 2017/00424* (2013.01); *A61B 2017/00526* (2013.01); *A61B 2017/320088* (2013.01); *B33Y 50/00* (2014.12); *Y02P 10/295* (2015.11)

(58) Field of Classification Search
CPC .... A61B 17/320068; A61B 17/320092; A61B 2017/00424; A61B 2017/00402; B23K 26/342; B33Y 10/00
See application file for complete search history.

(56) References Cited

U.S. PATENT DOCUMENTS

| | | |
|---|---|---|
| 5,322,055 A | 6/1994 | Davison et al. |
| 5,324,299 A | 6/1994 | Davison et al. |

(Continued)

FOREIGN PATENT DOCUMENTS

| | | |
|---|---|---|
| EP | 2982325 A1 | 2/2016 |
| WO | WO 2011/026164 A1 | 3/2011 |
| WO | WO 2016/123179 A1 | 8/2016 |

OTHER PUBLICATIONS

U.S. Appl. No. 14/976,047, filed Dec. 21, 2015.

(Continued)

*Primary Examiner* — Jermie Cozart
(74) *Attorney, Agent, or Firm* — Frost Brown Todd LLC

(57) ABSTRACT

A method of forming a component of an ultrasonic surgical instrument includes accessing a file including a digital model representing the component. The component includes a proximal portion and a distal portion. The proximal portion includes a contact portion. The distal portion includes an ultrasonic blade. The contact portion is configured to transmit ultrasonic vibrations to the ultrasonic blade when the component is acoustically coupled to a complementary portion of an acoustic waveguide of the ultrasonic surgical instrument. The file is used to fabricate the component via an additive manufacturing process. Once the component has been fabricated, the distal portion is secured to a distal end of the complementary portion of the acoustic waveguide.

19 Claims, 8 Drawing Sheets

(51) Int. Cl.
    *A61B 17/00*    (2006.01)
    *B33Y 50/00*    (2015.01)

(56) References Cited

U.S. PATENT DOCUMENTS

| | | |
|---|---|---|
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,773,444 B2 | 8/2004 | Messerly |
| 6,783,524 B2 | 8/2004 | Anderson et al. |
| 7,336,533 B2 | 2/2008 | Hunter et al. |
| 8,057,498 B2 | 11/2011 | Robertson |
| 8,461,744 B2 | 6/2013 | Wiener et al. |
| 8,532,807 B2 * | 9/2013 | Metzger ............ A61F 2/46 700/98 |
| 8,591,536 B2 | 11/2013 | Robertson |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2015/0080924 A1 | 3/2015 | Stulen et al. |
| 2015/0328840 A1 * | 11/2015 | Zachariasen ........ B29C 67/0088 700/98 |

OTHER PUBLICATIONS

U.S. Appl. No. 61/410,603, filed Nov. 5, 2010.

Pratt, Philip, et al. "Robust ultrasound probe tracking: initial clinical experiences during robot-assisted partial nephrectomy." International journal of computer assisted radiology and surgery 10.12 (2015): 1905-1913.

Seifarth, Christian, "Flexible mini-factory for local and customized production in a container," Sep. 1, 2013, retrieved from the internet on Nov. 1, 2018: https://cordis.europa.eu/docs/results/609/609146/final1-cassamobile-finalpublishablesummary-v1-0.pdf.

Thiesse, Frédéric, et al. "Economic implications of additive manufacturing and the contribution of MIS." Business & Information Systems Engineering 57.2 (2015): 139-148.

International Search Report and Written Opinion dated Oct. 12, 2017 for International Application No. PCT/US2017/041357, 14 pages.

\* cited by examiner

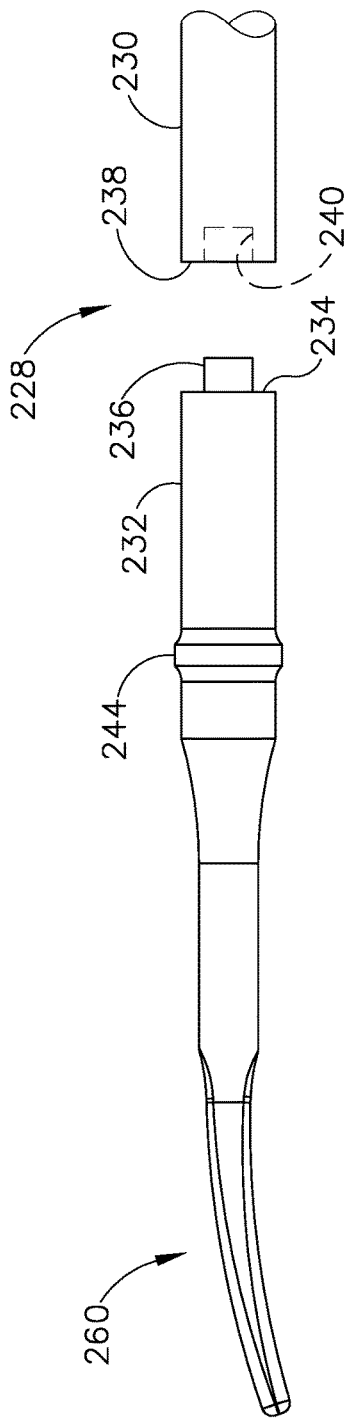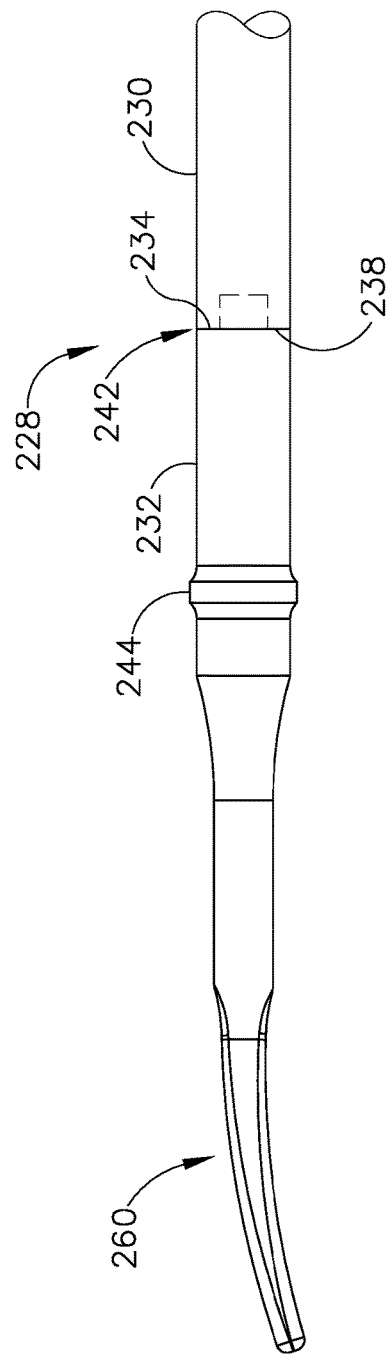

ULTRASONIC SURGICAL INSTRUMENT WITH AD HOC FORMED BLADE

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," the disclosure of which is incorporated by reference herein; and U.S. Pub. No. 2014/0114334, published Apr. 24, 2014, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5A depicts a top elevational view of the ultrasonic blade and distal waveguide portion of FIG. 4 disassembled from the proximal waveguide portion of FIG. 4;

FIG. 5B depicts a top elevational view of the ultrasonic blade and distal waveguide portion of FIG. 4 assembled with the proximal waveguide portion of FIG. 4;

Figure 1:
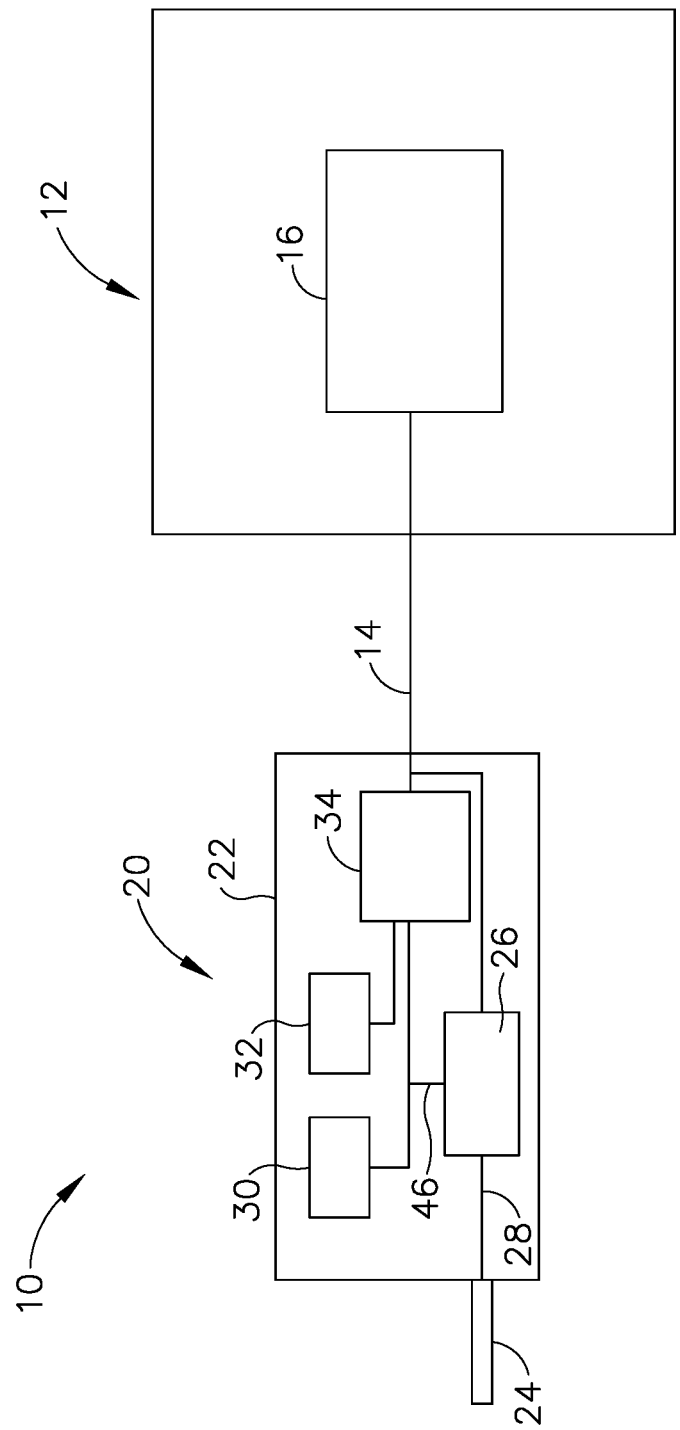
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). Some versions of system (10) may incorporate generator (12) into instrument (20), such that cable (14) may simply be omitted.

By way of example only, generator (12) may comprise the GEN04 or GEN11 sold by Ethicon Endo-Surgery, Inc. of Cincinnati, Ohio. In addition, or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

Those of ordinary skill in the art will understand that, as a matter of physics, the distal end of blade (24) is located at a position corresponding to an anti-node associated with resonant ultrasonic vibrations communicated through waveguide (28) (i.e., at an acoustic anti-node). When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 45 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
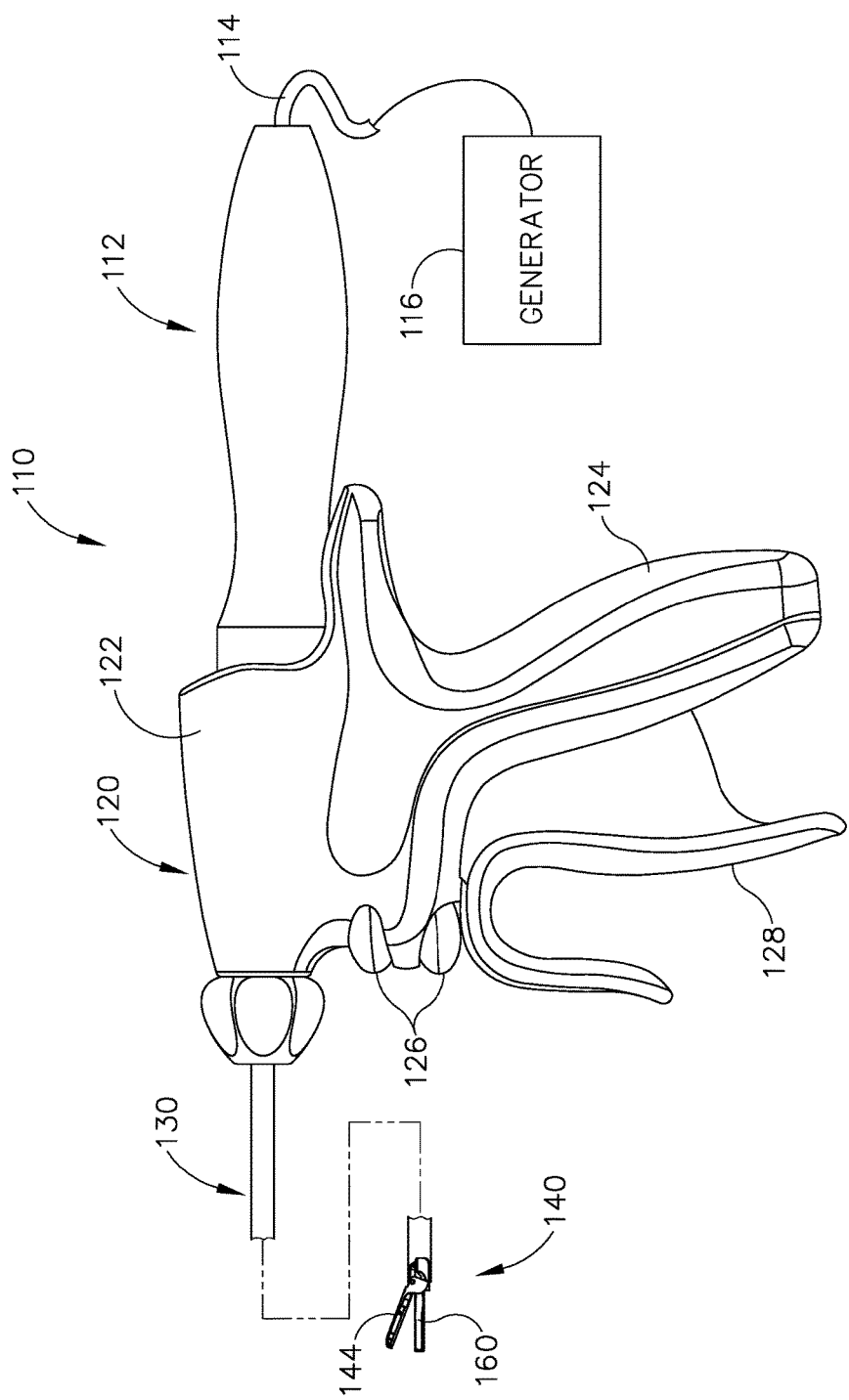
FIG. 2 depicts a side elevational view of an exemplary form that an instrument of the system of FIG. 1 may take.

FIG. 2 illustrates an exemplary ultrasonic surgical instrument (110). At least part of instrument (110) may be constructed and operable in accordance with at least some of the teachings of U.S. Pat. Nos. 5,322,055; 5,873,873; 5,980, 510; 6,325,811; 6,773,444; 6,783,524; 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, instrument (110) is operable to cut tissue and seal or weld tissue substantially simultaneously.

Instrument (110) of the present example comprises a handle assembly (120), a shaft assembly (130), and an end effector (140). Handle assembly (120) comprises a body (22) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is pivotably coupled with an inner tube (133) and an outer tube (132) (FIGS. 3 and 4) that form shaft assembly (130). Such an inner and outer tube configuration may be provided in accordance with the teachings of various references that are cited herein. Clamp arm (144) is further coupled with trigger (128). Trigger (128) is operable to drive one of the tubes of shaft assembly (130) longitudinally while the other tube of shaft assembly (130) remains stationary. This relative longitudinal movement between the tubes of shaft assembly (130) provides pivotal movement of clamp arm (144). Clamp arm (144) is thus pivotable toward ultrasonic blade (160) in response to pivoting of trigger (128) toward pistol grip (124); and clamp arm (144) is pivotable away from ultrasonic blade (160) in response to pivoting of trigger (128) away from pistol grip (124). Clamp arm (144) is thereby operable to cooperate with ultrasonic blade (160) to grasp and release tissue; and clamp arm (144) is further operable to compress tissue against ultrasonic blade (160) to thereby enhance the transfer of ultrasonic energy from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (126) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (44) and blade (160). In particular, activation of a second one of the buttons (126) may cause vibration of ultrasonic blade (160) at a relatively high amplitude. Other suitable operational modes that may be associated with buttons (126) will be apparent to persons skilled in the art in view of the teachings herein.

III. Exemplary Alternative Waveguide

Conventional waveguides (28) may be formed of a solid core of material as a single, monolithic piece. This construction may require surface features to be formed using a lathe and/or milling process, which may result in wasted material. In addition to providing a time consuming manufacturing process, this may also be costly with respect to the loss of material that is removed from a block of material during the formation process. It may therefore be desirable to provide a construction of waveguide (28) that enables waveguide (28) to be formed more efficiently, reducing the amount of material that may be lost during the manufacturing process.

Moreover, it may be more desirable to provide a system and process by which a practitioner or clinical system may manufacture surgical components, ad hoc, in situ, in order to allow for customization of such instruments. In particular, this may enable a surgeon to easily have on hand an ultrasonic blade that is best suited for the particular surgical operation at hand. Such a system and process may reduce the costs of shipping and manufacturing, and obviate or reduce the need for packaging certain portions of such instruments. In addition, such a system and process may enable a clinical facility to have access to various components of surgical instruments and other medical devices, without requiring the clinical facility to maintain an inventory of such components.

Figure 3:
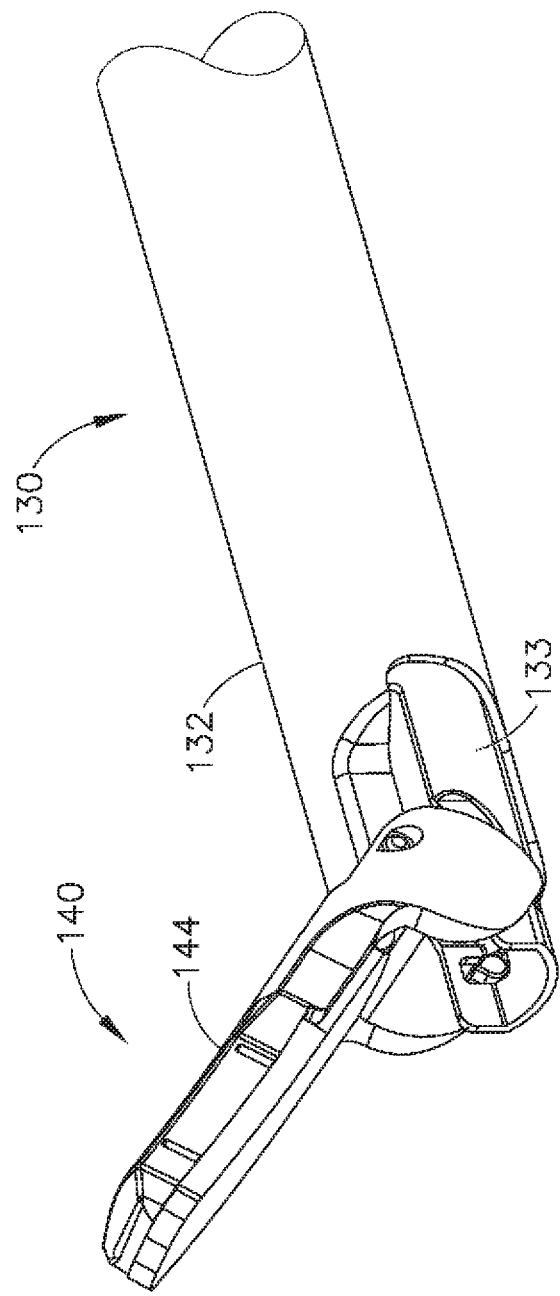
FIG. 3 depicts a perspective view of a distal portion of a shaft assembly of the instrument of FIG. 2, with an ultrasonic blade and distal waveguide portion removed.
Figure 4:
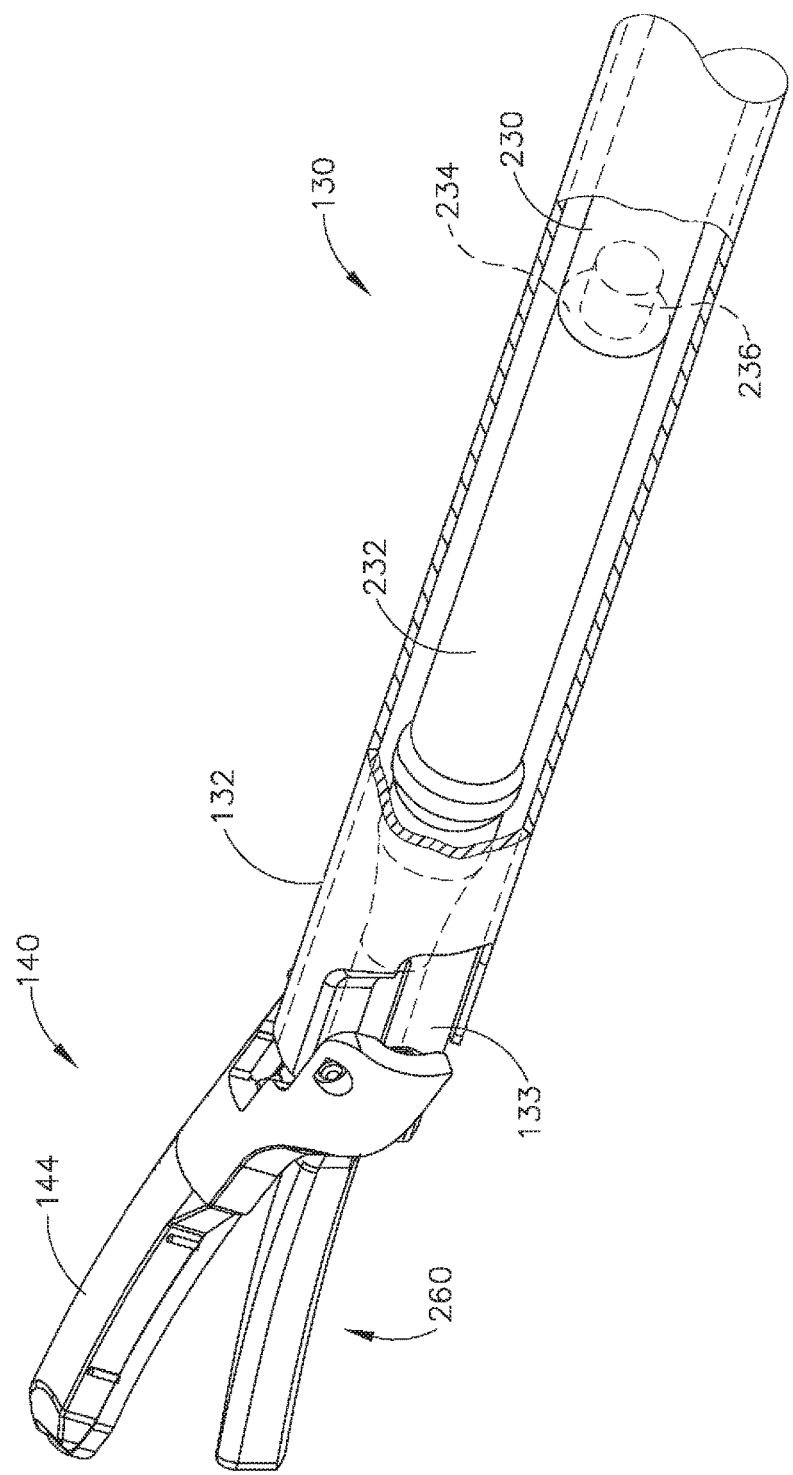
FIG. 4 depicts a perspective view of the distal portion of the shaft assembly of FIG. 3, with the ultrasonic blade and distal waveguide portion secured to a proximal waveguide portion.

FIGS. 4-5B show an exemplary alternative waveguide (228) that may be readily incorporated into instrument (20, 110), particularly, into an acoustic drivetrain of instrument (20, 110). Waveguide (228) thus represents an alternative form that waveguide (28) may take. Waveguide (228) of the present example includes a blade (260) that is operable to vibrate at ultrasonic frequencies in order to effectively cut through and seal tissue, particularly when the tissue is being compressed between blade (260) and another portion of an end effector, such as clamp arm (144) of end effector (140). It should be understood that the proximal end of waveguide (228) may be coupled with transducer assembly (112) to receive the ultrasonic vibrations that are ultimately applied to tissue via blade (260). As shown, rather than being a solid, unitary member, waveguide (228) of this example comprises a proximal portion (230) that is separately formed from a distal portion (232). Distal portion (232) is attached to proximal portion (230). As discussed in further detail below, instrument (110) or shaft assembly (130) may be included without distal portion (232) (see FIG. 3), or distal portion (232) may be attachable and detachable from instrument (20, 110), particularly from proximal portion (230).

As shown, distal portion (232) also includes blade (260) as an integral, unitary feature of distal portion (232). In the present example, blade (260) is substantially similar or identical to blade (160). However, it should be understood that the processes and features described herein may enable the formation of various different kinds of blades (160) having various different kinds of geometries and other structural features. Such variation may facilitate selection of a particular blade (260) configuration that is best suited to the particular surgical operation at hand.

In the present example, distal portion (232) of waveguide (228) also includes a first contact surface (234) and a projecting portion (236) extending proximally from the first contact surface (234). The distal end of proximal portion (230) includes a second contact surface (238) and a recess (240). In the example shown, in order to assemble waveguide (228), projecting portion (236) may be inserted into recess (240) until first contact surface (234) contacts or substantially abuts second contact surface (236) to thereby define an abutment or junction (242). In the present example, projecting portion (236) and recess (240) are configured to assemble in a press fit or interference fit manner. In other examples, however, projecting portion (236) and recess (240) may be assembled in various other suitable manners. For example, projecting portion (236) and recess (240) may include corresponding threads such that proximal and distal portions (230) may be threadably engaged. Other suitable manners of mechanically coupling proximal and distal portions (230, 232) will be apparent to persons skilled in the art in view of the teachings herein. Moreover, while in the present example there is no gap at the junction (242) between proximal and distal portions (230, 232) when they are coupled to one another, in other examples there may be a gap therebetween. As yet another merely illustrative alternative, the distal end of projecting portion (236) may engage the distal end of the recess (240), thus forming the abutting surfaces to communicate ultrasonic vibrations, such that first and second contact surface (234, 238) do not contact each other. Other suitable configurations of proximal and distal portions (230, 232) will be apparent to persons skilled in the art in view of the teachings herein.

In the present example, the acoustic drivetrain includes transducer assembly (112) and acoustic waveguide (228) (including blade (260)). Various suitable ways in which waveguide (228) may be mechanically and acoustically coupled with transducer assembly (112) will be apparent to those of ordinary skill in the art in view of the teachings herein. Transducer assembly (112) includes a set of piezoelectric discs (not shown) located proximal to a horn (not shown) of waveguide (260). The piezoelectric discs are operable to convert electrical power into ultrasonic vibrations, which are then transmitted along p portions (230, 232) of waveguide (280) to blade (260). By way of example only, this portion of the acoustic drivetrain may be operable in accordance with various teachings of various references that are cited herein.

It should be understood that waveguide (228) may be configured to amplify mechanical vibrations transmitted through waveguide (228). Furthermore, waveguide (228) may include features operable to control the gain of the longitudinal vibrations along waveguide (228) and/or features to tune waveguide (228) to the resonant frequency of the system. For example, waveguide (228) may include a plurality of notches, grooves, or other features (not shown) that are provided, at least in part, to assist in controlling the vibratory properties of waveguide (228). By way of example only, such features may include those described and shown in U.S. patent application Ser. No. 14/976,047, entitled "Ultrasonic Surgical Instrument with Tubular Acoustic Waveguide Segment," filed Dec. 21, 2015, published as U.S. Pub. No. 2017/0172607 on Jun. 22, 2017, the disclosure of which is incorporated by reference herein.

As best seen in FIGS. 5A-5B, waveguide (228) further includes an annular flange (244). Flange (244) is configured to receive an annular elastomeric seal (not shown). This elastomeric seal may engage the inner wall of an inner tube (not shown) that extends through shaft assembly (130), such that the seal and flange (244) may cooperate to provide structural support to waveguide (228). In other words, the seal and flange (244) may cooperate to prevent waveguide (228) from undesirably deflecting laterally within the inner tube, particularly when blade (260) encounters lateral loads from being pressed against tissue. The seal and flange (262) thus cooperate to prevent waveguide (228) from contacting the inner tube of shaft assembly (130). It should be understood that waveguide (228) may include a series of elastomeric seals that are spaced apart along the length of waveguide (228) for the same purpose, in accordance with configurations that will be apparent to those of ordinary skill in the art in view of the teachings herein.

In the present example, junction (242) is located at a position corresponding to a node associated with resonant ultrasonic vibrations communicated through waveguide (228). Flange (244) is also located at a position corresponding to a node associated with resonant ultrasonic vibrations communicated through waveguide (228). Alternatively, junction (242) and/or flange (244) may be located at any other suitable position(s) in relation to nodes/anti-nodes of resonant ultrasonic vibrations communicated through waveguide (228).

When transducer assembly (112) is energized, the distal end of blade (260) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through each portion (230, 232) of waveguide (228) to reach blade (260), thereby providing oscillation of blade (260) at the resonant ultrasonic frequency. Thus, when tissue is secured between blade (260) a clamp pad on clamp arm (144), for example, the ultrasonic oscillation of blade (260) may simultaneously sever the tissue and denature the proteins in adjacent tissue cells, thereby providing a coagulative effect with relatively little thermal spread. In some versions, an electrical current may also be provided through blade (260) and clamp arm (144) to also cauterize the tissue.

While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, various suitable ways in which waveguide (228) may be configured will be apparent to those of ordinary skill in the art in view of the teachings herein.

In the present example, proximal portion (230) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials. Proximal portion (230) may be made from one or more typical subtractive manufacturing or machining techniques, such as milling. In the present example, however, distal portion (232) is made from one or more additive manufacturing ("AM") (also known as "three-dimensional (3D) printing") techniques, as described in further detail below. However, in other examples, both proximal and distal portions (230, 232) and other portions of instrument (20, 110) may be manufactured by one or more AM techniques.

IV. Method of Assembling a Surgical Instrument

Surgical instruments may be manufactured, assembled, packaged, and shipped as a unit to a clinical facility and ready for use. In some instances, one component or several components may be manufactured by the manufacturer of the instrument (or another manufacturer), but may not be assembled, packaged and shipped with a particular instrument. In such instances, such component(s) may be assembled with the instrument at the clinical facility prior to a surgical procedure. Further, in some instances, certain portions of a surgical instrument are reusable, such that after a surgical procedure is completed, the reusable portions or components are cleaned and sterilized while the non-reusable components are discarded. Such non-reusable components may be kept in stock or shipped to the clinical facility as needed from a manufacturer or from a third party supplier.

In the present example, as discussed above, instrument (20, 110) may be manufactured, assembled, packaged, and shipped as a unit without distal portion (232) of waveguide (228) included in such unit. In other words, instrument (20, 100) may be provided with a shaft assembly configured as shown in FIG. 3, where distal portion (232) is omitted. Additionally, or alternatively, instrument (20, 110) may be initially manufactured, assembled, packaged, and shipped as a unit with distal portion (232) of waveguide (228) included in such unit. However, upon use of instrument (20, 110), it may be desirable to clean, sterilize, and reuse the remainder of instrument (20, 110), except for distal portion (232) of waveguide (228), which may be discarded and replaced.

Figure 8:
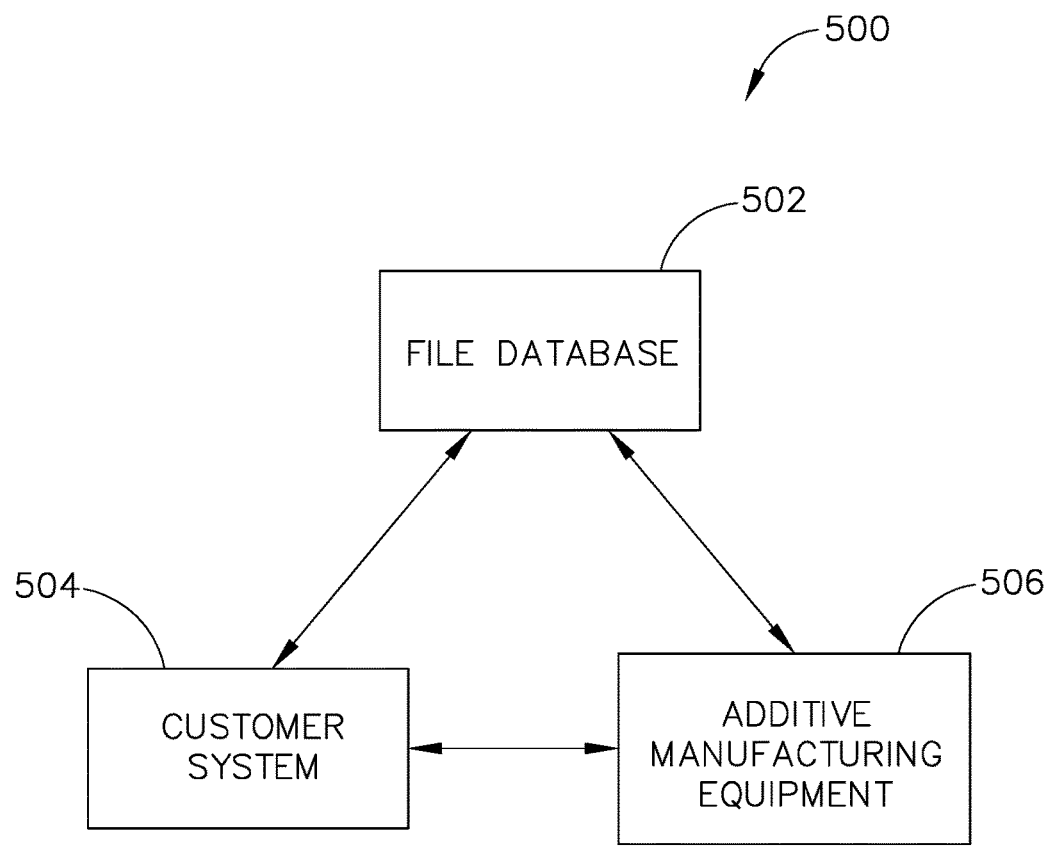
FIG. 8 depicts a schematic view of an exemplary system that is suitable for carrying out various methods of enabling ad hoc manufacture and assembly of surgical instruments.

In any instance, rather than receiving replacement distal portions (232) that are manufactured, packed, and shipped to the clinical facility, the clinical facility may utilize a manufacturing system that allows the clinical facility to, on an ad hoc or on demand basis, manufacture or 3D print needed parts or components. Referring to FIG. 8, such a manufacturing system (500) may include a file database (502) onto which parties such as manufacturers of component parts, or other parties, may upload files suitable for use in AM machines. The clinical facility's system (504) may be in communication with database (502). An AM system or machine (506), located at the clinical facility, may also be in communication with database (502); and with the clinical facility's system (504).

Database (502) may include a digital catalog of medical devices and components thereof that the clinical facility may access from the clinical facility's system (504). Such a digital catalog may include files of a type that are suitable for use with AM machines and processes, such as files in standard tessellation language (STL) format. Additionally, or alternatively, such a digital catalog may include files of various types or formats as will be apparent to persons skilled in the art in view of the teachings herein. In some examples, database (502) may include files that are incompatible with conventional AM processes or machines; or that otherwise may not be suited for use with AM processes or machines, such as typical computer aided design (CAD) files. In such examples, system (502) of the facility or healthcare system, and/or AM equipment (506) may be configured to convert such files into a suitable format, such as STL or other suitable formats.

In some examples, database (502) and the digital catalog associated therewith may be hosted on one or more remote servers, such as those controlled or owned by the manufacturer or another party. In other examples, the digital catalog may be stored directly on the clinical facility's system (504), such as one or more servers or computers on site at the clinical facility. The clinical facility's system (504) may also include at least one computer or other device including an interface that allows a user to interact with the digital catalog.

As shown in FIG. 8, and as noted above, manufacturing system (500) also includes at least one AM system or machine (506). In the present example, AM system or machine (506) comprises a direct metal laser sintering (DMLS) machine (e.g., such as those manufactured and sold by Stratasys, Ltd. (Eden Prairie, Minn.)). However, in other examples, AM system or machine (506) may include other types of AM machines, such as stereolithography (SLA), digital light processing (DLP), fused deposition modeling (FDM), selective laser sintering (SLS), selective laser melting (SLM), electron beam melting (EBM), and laminated object manufacturing (LOM). Other suitable types of AM machines and processes that may be utilized will be apparent to persons skilled in the art in view of the teachings herein.

It should also be understood that a single clinical facility may have more than one AM system or machine (506) located at the clinical facility, including more than one kind of AM system or machine (506) being located at the same clinical facility. In some instances, clinical sites associated with, for example, a healthcare or hospital system may include such additive manufacturing systems (506) in one location or a select few locations, such as a main hospital or facility. In some other instances, a healthcare or hospital system may have an off-site facility or location dedicated at least partially, or entirely to, AM for on demand production of surgical instrument components. Such a facility may be affiliated with a particular hospital system or a particular medical device manufacturer. Additionally, or alternatively, such facilities may be contract facilities, such that they provide medical components fabricated on demand to a variety of hospital systems, clinical facilities, and/or for a variety of medical device manufacturers. Other suitable arrangements will be apparent to those of ordinary skill in the art in view of the teachings herein.

Figure 6:
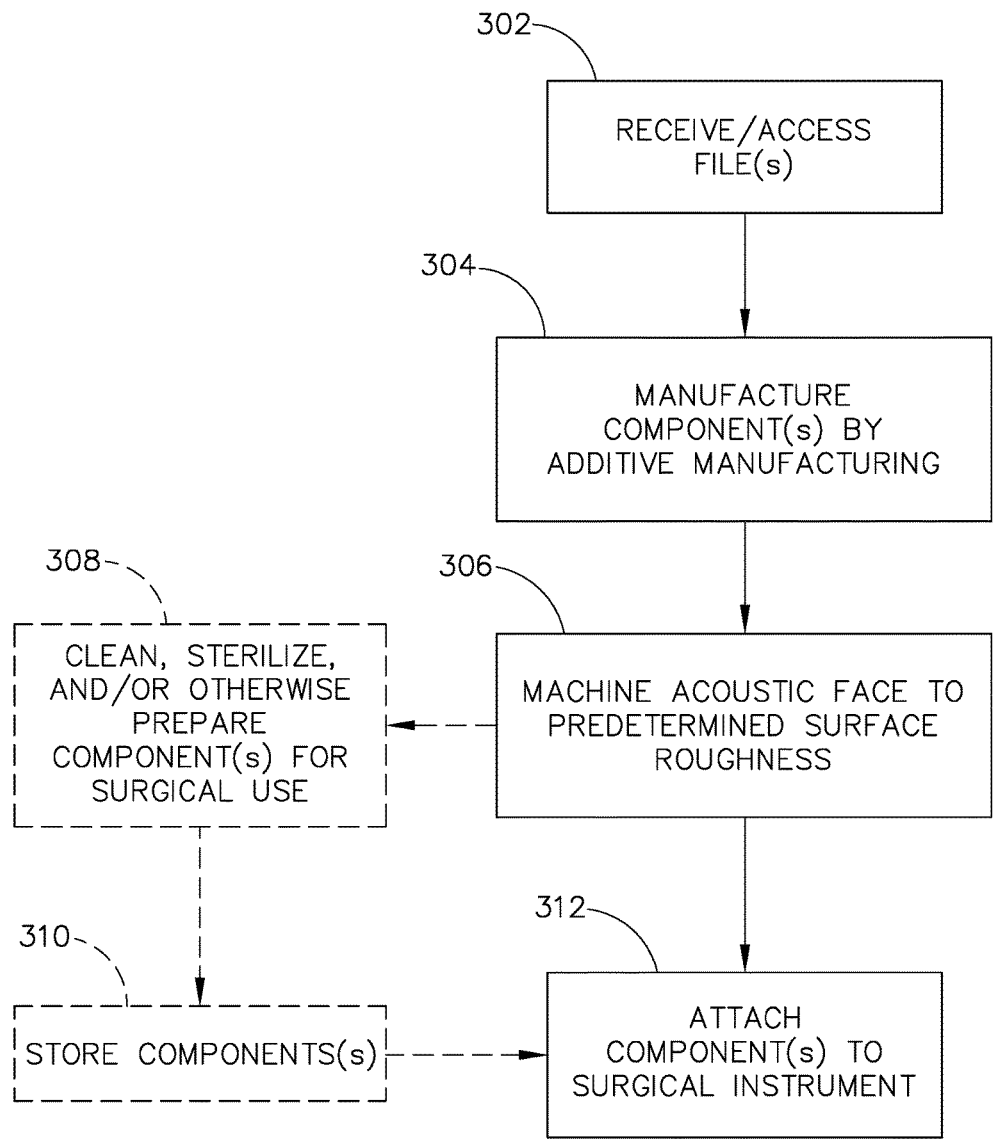
FIG. 6 depicts a flow chart showing various steps of an exemplary method for assembling a surgical instrument.

Referring to FIG. 6, in order to fabricate a component, such as distal portion (232) of waveguide (228), on demand and/or in situ, a clinical facility may receive or access files from a digital catalog, such as in database (502) discussed above (block 302). In some examples, the component that is desired to be manufactured may be selected using a part number associated therewith. In some examples, a user may input information about the particular instrument for which a part or component is needed, such as instrument (20, 110) described above. In some such examples, an instrument may include readable data that may be read by system (502) in order to determine which, if any, components may be fabricated and assembled with an instrument, such as instrument (110). In such examples, database (502) and/or system (504) may populate a list of appropriate components to be fabricated and assembled with instrument (20, 110).

In addition, or in the alternative, database (502) and/or system (504) may prompt the user to input or select a particular type of surgical procedure and/or other data that may assist in the database (502) and/or system (504) in presenting options to the user. In some examples, a user interface of system (504) may display to the user an image of such component(s) to be manufactured. Upon selecting a component to be manufactured, the system (504) may communicate data to AM equipment (506), such as at least one file suitable for AM, then direct the AM equipment (506) to manufacture the component (block 304).

In some examples where the component to be manufactured is distal portion (232), a method includes machining the component such that (and/or ensuring that) the first contact face (234) comprises a predetermined surface roughness that allows for the suitable transmission of ultrasonic vibrations from proximal portion (230) to distal portion (232), and thus to blade (160) (block 306). In some examples, an exemplary predetermined surface roughness is approximately root mean square (RMS) 32. In other examples, however, the predetermined surface roughness comprises between approximately RMS 36 and approximately RMS 64.

In the present example, the act of machining (block 306) is carried out using a piece of machining equipment (not shown) that is separate from AM equipment (506). By way of example only, the machining equipment may comprise a grinder, polisher, and/or other piece(s) of equipment as will be apparent to those skilled in the art in view of the teachings herein. In some such instances, the machining equipment may be automated such that the machining equipment is capable of automatically machining the AM-produced component, based on instructions received from database (502). It should therefore be understood that the machining equipment may form part of system (500) and may thus be in communication with database (502). In some other instances, AM equipment (506) is configured to fabricate the distal portion (232) such that the surface roughness of first contact face (234) has the predetermined surface roughness. In other words, some versions may not require a separate step of machining (block 306) by a separate piece of machining equipment.

In addition to or as an alternative to modifications relating to a predetermined surface roughness, some portions of the AM-produced component may be treated with a surface treatment in order for the AM-produced component to be suitable for intended use. Such surface treatments may include, but are not limited to, various mechanical, physical, and chemical treatments, such as machining, polishing, vapor smoothing, bead blasting, electroplating, etc. Other suitable surface treatments will be apparent to persons skilled in the art in view of the teachings herein.

In some examples, distal portion (232) may be fabricated in a manner that imparts particular surface characteristics to blade (260). For instance, in some examples of instrument (110), the clamp pad of clamp arm (144) is machined or otherwise treated to include teeth or other features to assist in the grasping of tissue between clamp arm (144) and blade (160, 260). Rather than adding such gripping features to the clamp pad, or in addition to adding such features to the clamp pad, such features, including teeth or the like, may be included on distal portion (232) during the AM process. For example, because AM processes, such as the ones described herein, create articles by depositing and creating layers of material, articles may be created along certain axes, each of which may result in different surface characteristics of the article. In the present example, distal portion (232) may be fabricated along a direction or axis such that edges are formed transverse or perpendicular to the axis of waveguide (228). Thus, the edges may act as gripping features and may obviate the need to machine or otherwise include such features in other components, such as clamp pad. However, it will be understood that distal portion (232) may be manufactured in a different manner resulting in varying surface characteristics of distal portion (232).

In some versions, the AM-produced component is cleaned, sterilized, or otherwise prepared for surgical use (block 308) according to suitable and typical methods carried out in a clinical environment, before or after the AM-produced component is determined to be suitable (e.g., mechanically, acoustically, etc.) for use. In some examples, once cleaned, sterilized or otherwise treated (block 308), the AM-produced component (e.g. distal portion (232)) may optionally be stored at the clinical facility or another location (block 310)). Once ready for use, distal portion (232) may be attached to instrument (20, 110) in a suitable manner (block 312), such as those described above, and the assembled instrument (20, 110) may be used to operate on tissue as described herein.

While instrument (20, 110) is provided in the present example, it should be understood that the teachings herein may be readily applied to various other kinds of instruments, including but not limited to instruments that would not be categorized as ultrasonic surgical instruments. Similarly, while distal portion (232) of waveguide (228) is described herein as a component that may be manufactured in an AM process, various other components that may be manufactured in an AM process will be apparent to those of ordinary skill in the art in view of the teachings herein.

V. Method of Enabling Ad Hoc Manufacture of Medical Device Components

Figure 7:
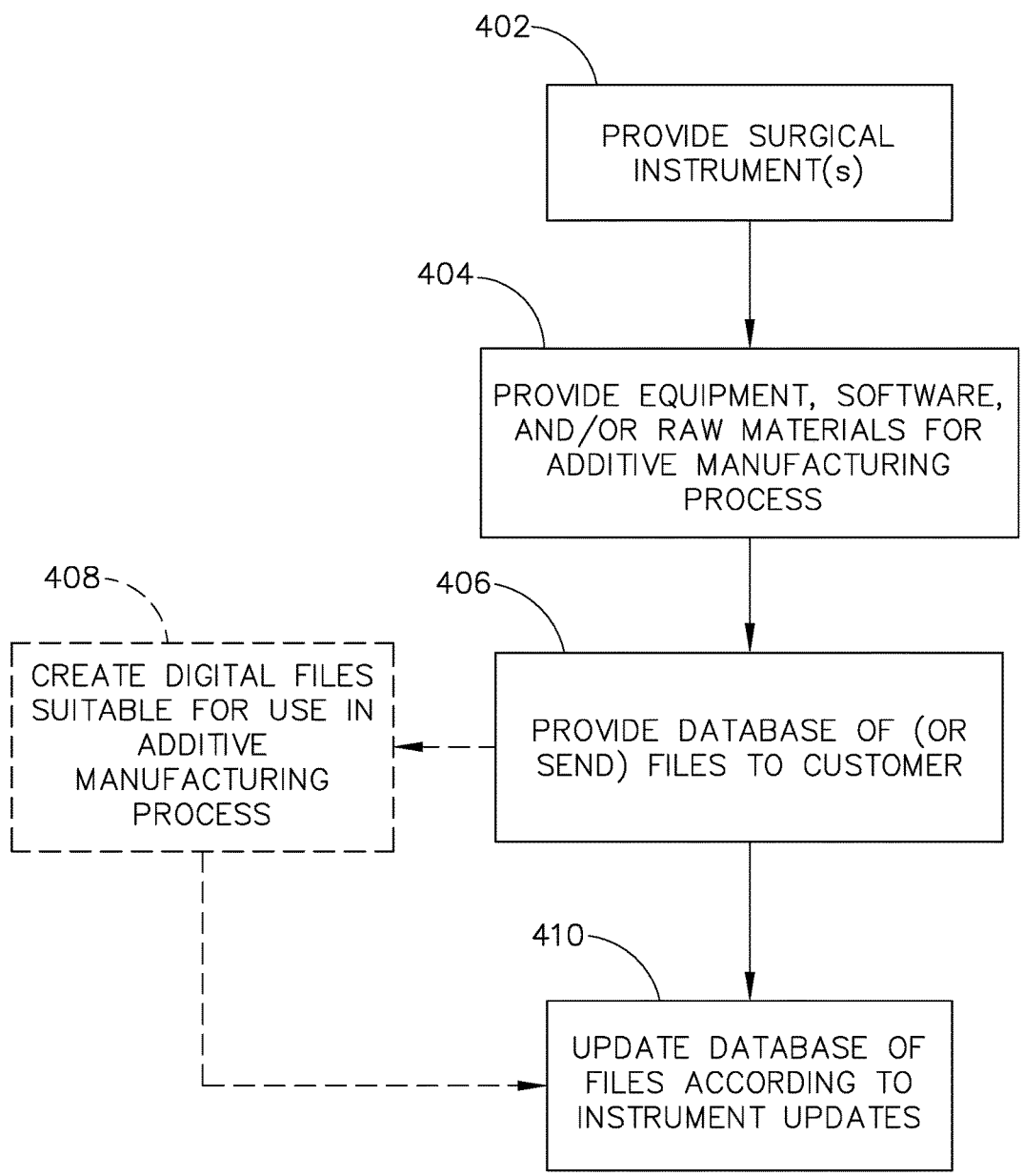
FIG. 7 depicts a flow chart showing various steps of an exemplary method for enabling ad hoc manufacture and assembly of surgical instruments.

FIG. 7 shows a method of enabling ad hoc or on demand manufacture of surgical instruments, medical devices, or components thereof. In some examples, such a method may include enabling the manufacture or fabrication of entire new surgical instruments or other medical devices; or only enabling the manufacture or fabrication of certain component(s) of surgical instruments or other medical devices. In some examples, such components may be manufactured to replace a component of an instrument that is replaceable or intended to be replaced after use. By way of example, as described herein, distal portion (232) of waveguide (228) is such a component that may be replaced after use of instrument (20, 110).

In the present example, a method of enabling ad hoc manufacture of medical device components includes providing at least one surgical instrument to a clinical facility or healthcare system associated therewith (block 402). Such a surgical instrument may include instrument (20, 110), but is not so limited. In some examples, the provision of surgical instruments step (block 402) may be in accordance with sales cycles of manufacturers and purchasing habits of clinical facilities such that it may occur well in advance of other steps described herein. Alternatively, in some examples, the provision of surgical instruments step (block 402) may be optional such that it may not necessarily occur. For example, a clinical facility or healthcare system may already have a stock of such surgical instruments or may obtain a surgical instrument from a party other than the manufacturer. Additionally, or alternatively, a clinical facility or healthcare system may have previously used instruments on hand or in stock that have been cleaned and sterilized for reuse. Such previously used instruments may be missing one or more components, with such components being capable of production via AM processes as described herein.

In the example shown, a manufacturer or other party may provide equipment, software, and/or raw materials suitable for use in an AM process (block 404), in order to enable the on demand fabrication of components. In some examples, such provision of equipment, software, and/or raw materials (block 404) is provided through a license to use such equipment, software, and/or raw materials. In other examples, such provision (block 404) may be through a sale of the equipment, software, and/or raw materials. In some examples, a party may provide the AM machine or equipment itself (block 404), such as machine (506) described above and any other associated equipment that may be used together with such AM equipment (such as computers, graphical user interfaces, etc.). Additionally, or alternatively, a clinical facility or healthcare system may possess or provide its own AM machine or equipment (e.g., machine (506)).

Moreover, in some examples, a party may provide software (block 404) associated with an AM machine (either provided by that party or the clinical facility or healthcare system). For example, such software may include code that directs the operation of the AM machine. In addition, or in the alternative, such software may be incorporated into the clinical facility or healthcare system's information technology systems (504) that enables the system (504) to interact with those of the manufacturer or other party.

In some examples, the manufacturer may provide one or more raw materials (block 404) that are suitable for an AM manufacturing process. The raw materials provided may vary according to the particular type of AM equipment (506) utilized, requirements of the manufactured component and/or instrument. In the present example, where the component to be manufactured includes distal portion (232), the raw material may include a Ti-6Al-4V powder that is suitable for use with an AM process. However, other suitable materials may be provided (block 404) and used according to the particular device or component being manufactured, including but not limited to other titanium alloys, aluminum alloys, sapphire, stainless steel, or any other acoustically compatible material or combination of materials.

In other examples, however, the manufacturer may not provide raw materials (block 404) to the clinical facility or healthcare system. For example, a third party, rather than the manufacturer, may provide the materials (block 404) to the clinical facility or healthcare system. Other suitable ways in which a clinical facility or healthcare system may be provided with (block 404) or obtain raw materials that are suitable for use with an AM process will be apparent to persons skilled in the art in view of the teachings herein.

Regardless of the source of equipment, software, and/or raw materials, a party such as a manufacturer may provide a database including files, or may send or otherwise provide access to files, to the clinical facility or healthcare system (block 406). In the present example, the manufacturer provides such access to a file or files (block 406) that are suitable for aiding in or causing the manufacturing of distal portion (232) with an AM process. For example, such file(s) may include at least one digital model representing the component and software code for controlling an AM machine (506). In the present example, a manufacturer provides a database, such as in the manner described above with respect to database (502) herein. In additional or alternative examples, a manufacturer may provide files (block 406) suitable for an AM process in a different manner, such as communicating or sending files to system (504) or AM equipment (506) itself, to certain parties through electronic mail, via a physical storage device (such as a compact disk or external drive), or in various other suitable manners in which to communicate information or data, as will be apparent to persons skilled in the art in view of the teachings herein.

In any of the examples, the files sent to the clinical facility (block 406) may be of a type that are suitable for use with AM machines and processes, such as files in standard tessellation language (STL) format or other various types or formats as will be apparent to persons skilled in the art in view of the teachings herein. In some examples, the manufacturer may send files (block 406) that are incompatible or not suited for use with AM processes or machines, such as typical computer aided design (CAD) files. In such examples, system (504) of the facility or healthcare system, and/or AM equipment (506) may be configured to convert such files into a suitable format, such as STL or other suitable formats. In some examples, however, such steps may be carried out by some party other than a manufacturer.

In some instances, it may be necessary or otherwise desirable to create additional files (block 408) that are suited for use in an AM process. Such additional files may be warranted to provide additional components for surgical instruments or medical devices; or to provide new configurations of otherwise conventional components for surgical instruments or medical devices. In either case, the additional files may be created (block 408) by a manufacturer of surgical instruments (20, 110), by a third party, or by someone associated with the clinical facility.

Various suitable ways in which such additional component files may be created (block 408) will be apparent to those of ordinary skill in the art in view of the teachings herein. By way of example only, such files may be created (block 408) by using various CAD applications that will be apparent to persons skilled in the art in view of the teachings herein. Thus, a manufacturer of instrument (20, 110) may create a CAD file of portions of instrument (20, 110), such as waveguide (228), or of distal portion (232), etc.

In addition, or in the alternative, such files may be created (block 408) by scanning an existing component of which a copy is desired to be made by an AM process. Additionally, or alternatively, an existing distal portion (232) or waveguide (228) may be scanned, such as by methods described below, to create a file suitable for use in an AM process. In an example where the entire waveguide is scanned, and it is desired to fabricate only distal portion (232) from an AM process, a party may use such a scanned file or data to create a file consisting of only of data or a digital model associated with the distal portion (232), incorporating such changes as needed to create distal portion (232). For example, a portion of scanned waveguide (228) may be modified with a CAD program in order to include projecting portion (236). Such scanning processes and systems may be carried out using various scanning and/or imaging methods, such as those utilizing semiconductor charge-coupled devices (CCD), complementary metal-oxide-semiconductor devices (CMOS), laser triangulation (rotational, slit, etc.), and/or devices utilizing stereoscopic, photometric, optical, electro-optical, structured light, and various other scanning or imaging methods and techniques, or combinations thereof. Other suitable scanning and/or imaging techniques will be apparent to persons skilled in the art in view of the teachings herein.

In some examples, files or data obtained from scanning an actual component may be converted into files appropriate for an AM process, such as STL or other suitable files. Moreover, in addition to creating such digital files, a party may update database (502) (block 410). For example, a manufacturer, upon instruments being updated or new features or components being added to an instrument or device, may update database (502) (block 410) to include such new features or components. Moreover, in some examples, a party may add or include components to database (502) that are custom or to be solely used with a particular clinical facility or healthcare system. Other suitable additions and updates to database (502) that parties may make will be apparent to persons skilled in the art in view of the teachings herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of forming a component of an ultrasonic surgical instrument, the method comprising: (a) accessing a file including a digital model representing the component, wherein the component comprises a proximal portion and a distal portion, wherein the proximal portion comprises a contact portion, wherein the distal portion comprises an ultrasonic blade, wherein the contact portion is configured to transmit ultrasonic vibrations to the ultrasonic blade when the component is acoustically coupled to a complementary portion of an acoustic waveguide of the ultrasonic surgical instrument; (b) using the file to fabricate the component via an additive manufacturing process; and (c) securing the proximal portion of the component to a distal end of the complementary portion of the acoustic waveguide.

Example 2

The method of Example 1, wherein the contact portion comprises a predetermined surface roughness, wherein the predetermined surface roughness is configured to enable the ultrasonic blade to vibrate at a predetermined vibratory frequency in response to the ultrasonic vibrations transmitted from the transducer.

Example 3

The method of Example 2, wherein the predetermined surface roughness is approximately 32 RMS.

Example 4

The method of any one or more of Examples 2 through 3, further comprising machining the contact portion to obtain the predetermined surface roughness.

Example 5

The method of any one or more of Examples 1 through 4, wherein accessing the file comprises accessing a database comprising a plurality of files.

Example 6

The method of any one or more of Examples 1 through 5, wherein the plurality of files comprises a plurality of standard tessellation language (STL) files.

Example 7

The method of claim 1, wherein the additive manufacturing process comprises direct metal laser sintering.

Example 8

The method of any one or more of Examples 1 through 7, wherein using the file to fabricate the component via an additive manufacturing process comprises utilizing a titanium alloy powder in the additive manufacturing process.

Example 9

The method of any one or more of Examples 1 through 8, wherein the titanium alloy powder comprises Ti-6Al-4V.

Example 10

The method of any one or more of Examples 1 through 9, wherein the step of using the file to fabricate the component via an additive manufacturing process is performed in a clinical facility.

Example 11

The method of any one or more of Examples 1 through 10, wherein accessing the file comprises obtaining a license to use the file for an additive manufacturing process.

Example 12

The method of any one or more of Examples 1 through 11, further comprising obtaining a raw material suitable for the additive manufacturing process.

Example 13

The method of Example 12, wherein the raw material comprises metal alloy powder.

Example 14

The method of any one or more of Examples 1 through 13, wherein the step of securing the proximal portion of the component to a distal end of the complementary portion of the acoustic waveguide comprises threading a threaded protrusion into a threaded recess.

Example 15

The method of any one or more of Examples 1 through 14, further comprising utilizing the ultrasonic surgical instrument to operate on tissue.

Example 16

A method of enabling ad hoc manufacturing of medical device components in a clinical setting, comprising: (a) creating a plurality of files that are suitable for use with an additive manufacturing process; (b) providing access to the files to at least one clinical facility or healthcare system; and (c) providing a portion of a medical device to the at least one clinical facility or healthcare system, wherein at least one of the files is associated with a digital model of a component configured to be incorporated with the portion of the medical device.

Example 17

The method of Example 16, wherein the medical device comprises an ultrasonic surgical instrument, wherein the component comprises a portion of a waveguide of the ultrasonic surgical instrument.

Example 18

A method of assembling an ultrasonic surgical instrument, the method comprising: (a) obtaining a portion of an ultrasonic surgical instrument, wherein the portion of the ultrasonic surgical instrument comprises a first portion of an acoustic waveguide, wherein the acoustic waveguide is configured to acoustically couple with a transducer assembly, wherein first portion of the acoustic waveguide comprises a first attachment portion at a distal end thereof; (b) fabricating a second portion of the acoustic waveguide with an additive manufacturing process in a clinical facility, wherein the second portion of the acoustic waveguide comprises an ultrasonic blade, wherein the second portion of the acoustic waveguide comprises a second attachment portion at a proximal end thereof; and (c) coupling the first and second attachment portions to thereby mechanically and acoustically couple the first and second portions of the acoustic waveguide in the clinical facility.

Example 19

The method of Example 18, wherein the first attachment portion comprises a recess, wherein the second attachment portion comprises a projection configured to fit within the recess.

Example 20

The method of any one or more of Examples 18 through 19, wherein fabricating the second portion comprises imparting ridges onto the ultrasonic blade

VII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A method of forming a component of an ultrasonic surgical instrument, the method comprising:
    (a) accessing a file including a digital model representing the component, wherein the component comprises a proximal portion and a distal portion, wherein the proximal portion comprises a contact portion, wherein the distal portion comprises an ultrasonic blade, wherein the contact portion is configured to transmit ultrasonic vibrations to the ultrasonic blade when the component is acoustically coupled to a complementary portion of an acoustic waveguide of the ultrasonic surgical instrument;
    (b) using the file to fabricate the component via an additive manufacturing process; and
    (c) securing the proximal portion of the component to a distal end of the complementary portion of the acoustic waveguide.

2. The method of claim 1, wherein the contact portion comprises a predetermined surface roughness, wherein the predetermined surface roughness is configured to enable the ultrasonic blade to vibrate at a predetermined vibratory frequency in response to the ultrasonic vibrations transmitted from the transducer.

3. The method of claim 2, wherein the predetermined surface roughness is approximately 32 root mean square (RMS).

4. The method of claim 2, further comprising machining the contact portion to obtain the predetermined surface roughness.

5. The method of claim 1, wherein accessing the file comprises accessing a database comprising a plurality of files.

6. The method of claim 1, wherein the plurality of files comprises a plurality of standard tessellation language (STL) files.

7. The method of claim 1, wherein the additive manufacturing process comprises direct metal laser sintering.

8. The method of claim 1, wherein using the file to fabricate the component via an additive manufacturing process comprises utilizing a titanium alloy powder in the additive manufacturing process.

9. The method of claim 1, wherein the titanium alloy powder comprises Ti-6Al-4V.

10. The method of claim 1, wherein the step of using the file to fabricate the component via an additive manufacturing process is performed in a clinical facility.

11. The method of claim 1, wherein accessing the file comprises obtaining a license to use the file for an additive manufacturing process.

12. The method of claim 1, further comprising obtaining a raw material suitable for the additive manufacturing process.

13. The method of claim 12, wherein the raw material comprises metal alloy powder.

14. The method of claim 1, wherein the step of securing the proximal portion of the component to a distal end of the complementary portion of the acoustic waveguide comprises threading a threaded protrusion into a threaded recess.

15. The method of claim 1, further comprising utilizing the ultrasonic surgical instrument to operate on tissue.

16. A method of enabling ad hoc manufacturing of medical device components in a clinical setting, comprising:
    (a) creating a plurality of files that are suitable for use with an additive manufacturing process;
    (b) providing access to the files to at least one clinical facility or healthcare system; and
    (c) providing a portion of a medical device to the at least one clinical facility or healthcare system, wherein at least one of the files is associated with a digital model of a component configured to be incorporated with the portion of the medical device;
    wherein the medical device comprises an ultrasonic surgical instrument, and wherein the component comprises a portion of a waveguide of the ultrasonic surgical instrument.

17. A method of assembling an ultrasonic surgical instrument, the method comprising:
    (a) obtaining a portion of an ultrasonic surgical instrument, wherein the portion of the ultrasonic surgical instrument comprises a first portion of an acoustic waveguide, wherein the acoustic waveguide is configured to acoustically couple with a transducer assembly, wherein first portion of the acoustic waveguide comprises a first attachment portion at a distal end thereof;
    (b) fabricating a second portion of the acoustic waveguide with an additive manufacturing process in a clinical facility, wherein the second portion of the acoustic waveguide comprises an ultrasonic blade, wherein the second portion of the acoustic waveguide comprises a second attachment portion at a proximal end thereof; and (c) coupling the first and second attachment portions to thereby mechanically and acoustically couple the first and second portions of the acoustic waveguide in the clinical facility.

18. The method of claim 17, wherein the first attachment portion comprises a recess, wherein the second attachment portion comprises a projection configured to fit within the recess.

19. The method of claim 17, wherein fabricating the second portion comprises imparting ridges onto the ultrasonic blade.

* * * * *